March 12, 1963 G. C. LOTHROP Plant Pat. 2,241
ROSE PLANT
Filed Dec. 21, 1961
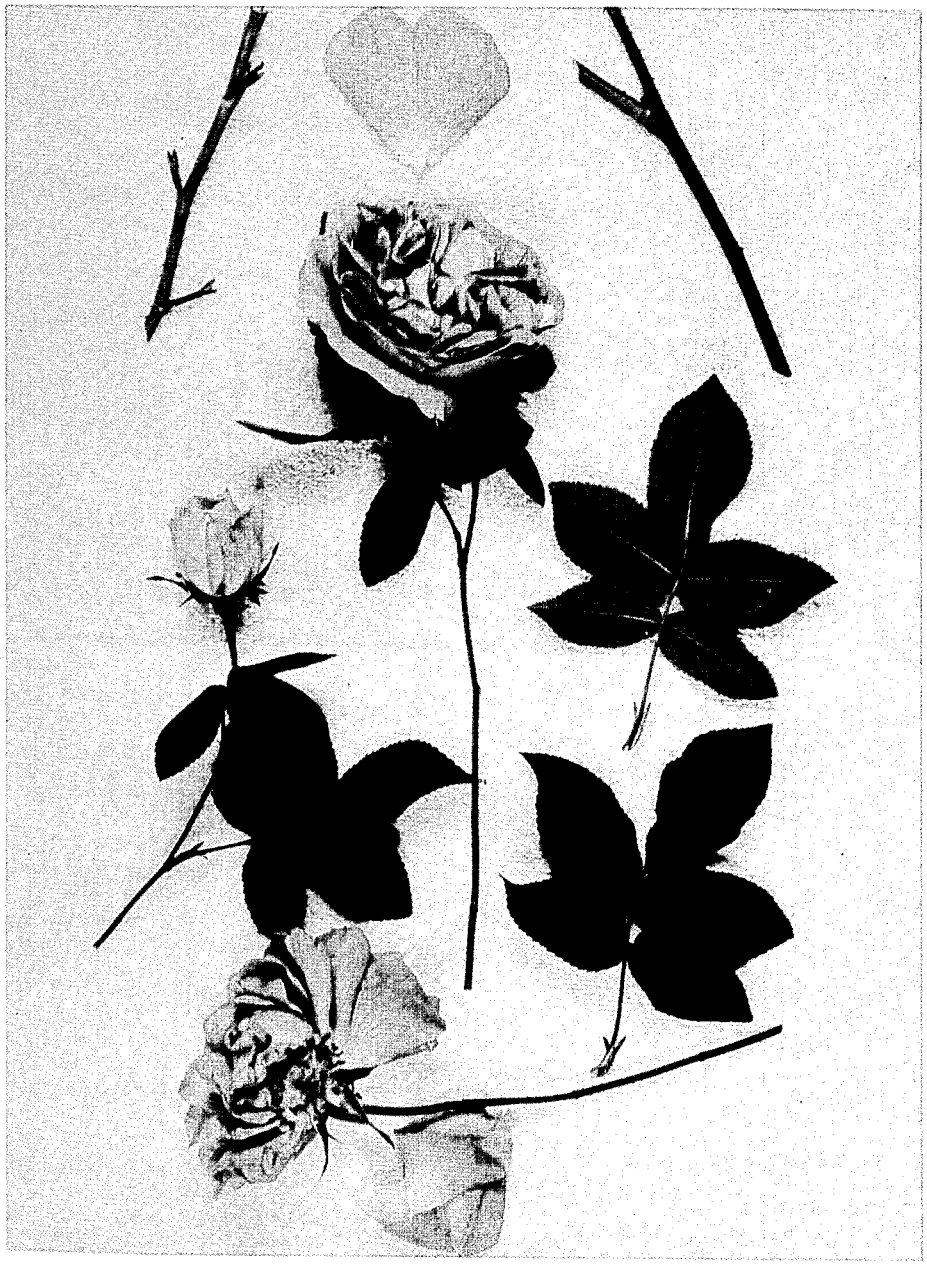
INVENTOR;
GROVER C. LOTHROP
BY Merchant, Merchant & Gould
ATTYS United States Patent Office Plant Pat. 2,241
Patented Mar. 12, 1963

2,241
ROSE PLANT
Grover C. Lothrop, Corona, S. Dak.
Filed Dec. 21, 1961, Ser. No. 161,324
1 Claim. (Cl. 47—61)

The present invention relates to a new and distinct variety of rose plant having characteristics of both *Rosa rugosa* and the hybrid tea class, and which originated as a seedling found in a cultivated area.

This new rose results from a seedling selected in 1953 from a cultivated site where *rugosa* hybrids had been crossed with hybrid tea roses for a rose breeding project at Hartford Beach, South Dakota, the chief objectives of the breeding project being winter hardiness and the development of high quality rose plants. With respect to the supposed seed parent of this new variety, the most definite information ascertainable when the seedling was discovered is that the supposed seed parent would be from Hansen's hybrid *rugosa* roses. This new variety has blossomed for four (4) consecutive years in its present location in South Dakota with consistent characteristics. The following unique combination of characteristics are outstanding in this new variety and distinguish it from its parents as well as from all other varieties of which I am aware:

(1) Entirely thornless;

(2) Extreme winter hardiness without special winter protection;

(3) The Spinel Pink general color tonality of the flowers, which change to Light Rosolome Purple;

(4) Good flower production;

(5) Attractive and heavy foliage with an open habit of growth;

(6) Lasting and distinct fragrance.

Although the above distinguishing characteristics were established on the plant when found in its original cultivated location, subsequent asexual reproduction of this new variety by cuttings, as performed at Hartford Beach, South Dakota, at the Horticulture Department of the South Dakota Experiment Station, and also at Brookings, South Dakota, shows that the characteristics and distinctions thereof run true to form and are established and transmitted through succeeding propagations.

The following is a detailed description of my new variety, with color terminology in accordance with Ridgway's Color Standards and Nomenclature, except where general color terms of ordinary dictionary significance are obvious.

*Flower*

(Observations made from a plant grown outdoors in the month of July, at Hartford Beach, South Dakota and from plants grown outdoors and in the greenhouse in April and May at Brookings, South Dakota.)

Blooming habit: Single crop, June and July.
Flowers borne: Usually singly but sometimes 2–3 to a stem.
Quantity of bloom: Moderate to heavy.
Fragrance: Of a very fragrant and lasting nature.
Peduncle: Erect, average length, almost smooth, Apple Green, Plate XVII (Ridgway).
Bud, before calyx breaks: Size—medium. Form—round or oblong.
As calyx breaks: Color—Light Dull Green Yellow, Plate XVII, 27′ G.Y. (Ridgway).
Sepals: Moderately smooth, terminal is lance-like, margins have foliaceous appendages.
Bloom:
*Size.*—Average 3½ to 4 inches in diameter by 2½ inches deep.

*Petalage.*—Double, 50 or more under normal growing conditions.
*Form.*—Round-oblate when mature, slightly cupped on opening.
Petals:
*Texture.*—Medium thickness. Dull.
*Shape.*—Obovate, with apex depressed.
*Color.*—Freshly opened-Spinel Pink, Plate XXVI (Ridgway). Then changing to Light Rosolome Purple. Color fairly uniform on both sides, extending well to the base. Slight color change with age. When petals drop after 7–10 days they are Cameo Pink, Plate XXVI (Ridgway).
Venation: Veins are visible and darker on inner surface.
Lasting quality: On plant, 7–10 days. Cut flowers with long stems, 10–12 days.

*Genital Organs*

Stamens: Many, regular arrangement.
Filament: Average to long, 8–10 mm., Pale Dull Green-Yellow, Plate XVII (Ridgway).
Anthers: Large, opening uniformly. Color—Wax Yellow, Plate XVI (Ridgway). Pollen-abundant, Strontian Yellow, Plate XVI (Ridgway).
Pistil: Many, Apple-Green color, Plate XVII (Ridgway).
Style: Even, short, average caliper.
Stigma: Color—Dull Green-Yellow, Plate XVII (Ridgway).
Ovaries: Enclosed in calyx.
Hips: Regular, average size, moderately smooth.
Seeds: Many, 35–50, small.

*Plant*

Bush type, medium to small. Extreme winter hardiness. It has been growing without protection for five years and has shown no apparent injury. The United States Weather Bureau Station 14 miles away reports minimum temperatures of 20 degrees below zero F., or colder each winter. Leaf fungous diseases such as mildew and blackspot have never been observed on the plants growing without chemical protection, although other roses, such as "Garden Party," "Golden Rapture," and "Pink Delight," which were growing nearby were severely infected by such diseases. The foliage is heavy and fairly dense making it an attractive shrub when not in bloom. It grows to a height of 2½ feet with an open habit of growth. There is no trace of thorns on stems or leaf petioles. Numerous prickles are present on the stems of new growth; however, the prickles disappear as the new growth ages.

Stems: The canes are a Forest-Green color, Plate XVII (Ridgway), with a light pubescence which becomes less noticeable with age. Canes as well as leaf petioles are entirely free of thorns. There are many stems attached to the crown and these are small in diameter. (⅜ inch.)
Foliage: The pinnate leaves are Elm-Green color, Plate XVII (Ridgway), on the upper surface and have a gray green lower surface color. Their average size is 3½ x 4½ inches with leaflets 1¼ x 2 inches. The upper leaf surface is smooth but dull colored with serrated margin. Veins and mid-rib are prominent.
Blossoms: The blossoms are usually borne singly on a long stem and last 7–10 days on the plant. The buds are round, and mature blossoms are round-oblate. Petals are deep pink and number fifty or more per blossom. The blossoms have a distinct fragrance. At maturity they measure as much as 4 inches in diameter and 2½ inches deep. At the above referred to South Dakota locations the blossom period is generally from June 10th to July 1st. The petals persist for 7–10 days.

I claim:

A new and distinct variety of rose plant substantially as herein shown and described, characterized particularly as to novelty by the unique combination of being entirely thornless, extreme winter hardiness without special winter protection, a Spinel Pink general flower color tonality which changes to Light Rosolome Purple, a good flower production, attractive and heavy foliage with an open habit of growth, and blossoms having a lasting and distinct fragrance.

No references cited.